United States Patent
Zheng et al.

(10) Patent No.: US 12,274,837 B2
(45) Date of Patent: Apr. 15, 2025

(54) CATHETER FIXING ASSEMBLY

(71) Applicant: Solventum Intellectual Properties Company, Maplewood, MN (US)

(72) Inventors: Yang Zheng, Shanghai (CN); Ce Shang, Shanghai (CN); Haiping Cao, Shanghai (CN); Jun Nie, Shanghai (CN); Dan Wang, Shanghai (CN); Yue Chen, Shanghai (CN)

(73) Assignee: Solventum Intellectual Properties Company, Maplewood, MN (US)

( * ) Notice: Subject to any disclaimer, the term of this patent is extended or adjusted under 35 U.S.C. 154(b) by 790 days.

(21) Appl. No.: 17/294,301

(22) PCT Filed: Nov. 22, 2019

(86) PCT No.: PCT/IB2019/060080
§ 371 (c)(1),
(2) Date: May 14, 2021

(87) PCT Pub. No.: WO2020/109951
PCT Pub. Date: Jun. 4, 2020

(65) Prior Publication Data
US 2022/0008694 A1    Jan. 13, 2022

(30) Foreign Application Priority Data
Nov. 30, 2018   (CN) .......................... 201811455537.1

(51) Int. Cl.
*A61M 25/02*   (2006.01)

(52) U.S. Cl.
CPC ..... *A61M 25/02* (2013.01); *A61M 2025/0206* (2013.01); *A61M 2025/0246* (2013.01); *A61M 2025/0253* (2013.01)

(58) Field of Classification Search
CPC .......... A61M 25/02; A61M 2025/0206; A61M 2025/0246; A61M 2025/0253; A61M 2025/024
See application file for complete search history.

(56) References Cited

U.S. PATENT DOCUMENTS 6,224,571 B1 * 5/2001 Bierman ............... A61M 25/02
                                                                604/174
6,283,945 B1 * 9/2001 Bierman ............... A61M 25/02
                                                                604/174
(Continued)

FOREIGN PATENT DOCUMENTS

CN     203355089 U  * 12/2013
CN     204158864 U  *  2/2015
(Continued)

OTHER PUBLICATIONS

CN 205252274U Description Machine Translation (Year: 2016).*
International Search report for PCT International Application No. PCT/IB2019/060080 mailed on Feb. 18, 2020, 5 pages.

*Primary Examiner* — William R Carpenter
*Assistant Examiner* — Robert F Allen

(57) ABSTRACT

A catheter fixer is disclosed that comprises a base (1) and wing fixing portions (2). The base comprises an adhering surface and a fixing surface (11), and the adhering surface is configured to adhere the base to the skin. The wing fixing portions are configured to detachably fix wings on the fixing surface. The wings of the catheter are fixed to the base through the wing fixing portions, and an adhesive tape is disposed on a side of the base facing the skin, such that the adhesive tape is prevented from being adhered to the catheter, thereby avoiding leaving adhesive tape residue on the catheter.

19 Claims, 3 Drawing Sheets

(56) References Cited

U.S. PATENT DOCUMENTS

| | | | |
|---|---|---|---|
| 6,361,523 B1* | 3/2002 | Bierman | A61M 25/02 604/174 |
| 6,582,403 B1* | 6/2003 | Bierman | A61M 25/02 604/174 |
| 7,806,873 B2* | 10/2010 | Dikeman | A61M 25/02 604/174 |
| 8,211,064 B2 | 7/2012 | Sloan | |
| 9,526,869 B2 | 12/2016 | Beran | |
| 11,090,219 B1* | 8/2021 | Hayman | A61N 5/0616 |
| 2001/0039399 A1* | 11/2001 | Bierman | A61M 25/02 604/177 |
| 2002/0068904 A1* | 6/2002 | Bierman | A61M 25/02 604/180 |
| 2006/0015072 A1* | 1/2006 | Raulerson | A61M 25/02 604/533 |
| 2006/0276752 A1* | 12/2006 | Bierman | A61M 25/02 604/174 |
| 2007/0142784 A1* | 6/2007 | Dikeman | A61M 25/02 604/174 |
| 2007/0219500 A1* | 9/2007 | Wright | A61M 25/02 604/174 |
| 2007/0265572 A1* | 11/2007 | Smith | A61M 25/02 604/174 |
| 2008/0132848 A1* | 6/2008 | Wright | A61M 25/01 604/174 |
| 2008/0171993 A1 | 7/2008 | Beran | |
| 2009/0326473 A1* | 12/2009 | Rosenberg | A61M 25/02 604/174 |
| 2010/0016801 A1* | 1/2010 | Rosenberg | A61M 25/02 604/174 |
| 2012/0136314 A1* | 5/2012 | Ciccone | A61M 25/02 604/174 |
| 2012/0143140 A1* | 6/2012 | Bierman | A61M 25/02 604/174 |
| 2012/0197202 A1 | 8/2012 | Wright | |
| 2013/0079721 A1* | 3/2013 | Mizoguchi | A61M 25/02 604/174 |
| 2013/0079722 A1* | 3/2013 | Makino | A61M 25/02 604/174 |
| 2014/0142538 A1* | 5/2014 | Hyman | A61F 13/05 604/500 |
| 2015/0073347 A1* | 3/2015 | Friedrich | A61M 25/02 604/180 |
| 2017/0086746 A1* | 3/2017 | Ofek | A61B 5/746 |
| 2017/0120000 A1* | 5/2017 | Osypka | A61M 39/20 |

FOREIGN PATENT DOCUMENTS

| | | | |
|---|---|---|---|
| CN | 205055144 | | 3/2016 |
| CN | 205252274 | | 5/2016 |
| CN | 107224658 | | 10/2017 |
| CN | 217510932 U | * | 9/2022 |
| EP | 1549375 | | 7/2005 |
| JP | 2017-164257 | | 9/2017 |
| WO | WO 1997-015337 | | 5/1997 |
| WO | 200162328 A1 | | 8/2001 |
| WO | WO 2007-082093 | | 7/2007 |
| WO | WO 2008-054761 | | 5/2008 |
| WO | WO 2010-002393 | | 1/2010 |
| WO | 2013109835 A1 | | 7/2013 |
| WO | WO 2015/020882 | | 2/2015 |

* cited by examiner

CATHETER FIXING ASSEMBLY

TECHNICAL FIELD

The present disclosure relates to medical supplies, and in particular, to a catheter fixing assembly.

BACKGROUND

Currently, when a central venous catheterization procedure is performed, e.g. peripherally inserted central catheter (PICC) and central venous catheter (CVC), a catheter needs to be secured in place to prevent catheter displacements or even unplanned catheter withdrawals. Common catheter fixation methods include adhesive tape fixation and suture fixation. When an adhesive tape is used for fixation, the adhesive tape would leave adhesive tape residue on the catheter, making the site prone to bacterial growth, and potentially causing phlebitis and other issues. A suture fixation refers to suturing wings of the catheter directly to the skin. This technique, however, may cause pain or even tissue inflammation. In addition to the aforementioned methods, catheter fixers can be found in the prior art. However, these fixers come in a variety of models due to the diversity of shapes and sizes of catheters; selecting the right fixer thus becomes more difficult. Moreover, the overall space taken up by catheter fixers in the inventory is also increased due to the number of different catheters stored.

As a result, a sterile catheter fixer that continues to be sought after in this field is one that leaves no adhesive tape residue, incurs no damage to the skin when removed, can be effectively secured, and is applicable to different catheters.

SUMMARY

The disclosed catheter fixer at least partially solves the existing problems of adhesive tape residue or skin damage during removal.

The disclosed catheter fixing assembly is configured to fix a catheter. The catheter is provided with a catheter fixing wing, the catheter fixing wing comprising a fixing wing body and wings disposed on two sides of the fixing wing body. The catheter fixing assembly comprises a base and wing fixing portions. The base comprises an adhering surface and a fixing surface. The adhering surface is configured to adhere the base to the skin. The wing fixing portions are configured to detachably fix the wings on the fixing surface.

A central area on the fixing surface is provided with a groove configured to accommodate the fixing wing body, such that the wings can be accommodated by areas of the fixing surface at two sides of the groove.

In one embodiment, rotation shafts are included and vertically disposed on the areas of the fixing surface at two sides of the groove. The wing fixing portions are rotatably connected to the rotation shafts. When the wing fixing portions are rotated to a first position, the wings can be separated from the catheter fixing assembly. When the wing fixing portions are rotated to a second position, the wing fixing portions are superposed on the wings to fix the wings on the fixing surface.

The wing fixing portion is provided with a through hole, the diameter of the through hole corresponds to the diameter of the rotation shaft, the through hole has an opening at one side thereof, an opening of an orthogonal projection of the opening on an axial section of the through hole is smaller than the diameter of the rotation shaft; during assembling, the rotation shaft enters the wing fixing portion through the opening by deformation of material under a force.

The base is provided with snaps, the wing fixing portions are provided with slots, and the snaps are engaged to the slots when the wing fixing portions are rotated to the second position, thus fixing the wing fixing portions to the base.

The wing fixing portions are further provided with protrusions configured to be grabbed to release the engagement between the snaps and the slots when the wing fixing portions is away from the second position.

One side of the wing fixing portion facing the fixing surface is provided with a wing accommodation slot configured to accommodate the wing when the wing fixing portion is rotated to the second position.

The areas of the fixing surface at two sides of the groove are provided with limiting columns configured to match with round holes on the wings to limit positions of the wings when the wing fixing portions are rotated to the second position.

The wing accommodation slot is provided with multiple pressing portions configured to be in contact with the fixing wing and to incur deformation under compression when the wing fixing portion is rotated to the second position.

There are multiple pressing portions; orthogonal projections of the multiple pressing portions on the fixing surface are located in positions close to the groove.

The adhering surface is provided with an adhesive tape configured to adhere the base to the skin.

In one embodiment, the catheter fixer comprises a base and wing fixing portions. The base comprises an adhering surface and a fixing surface; the adhering surface is configured to adhere the base to the skin; and the wing fixing portions are configured to detachably fix wings on the fixing surface. The wings of the catheter are fixed to the base through the wing fixing portions. An adhesive tape is disposed on one side of the base facing the skin, such that the adhesive tape is prevented from being adhered to the catheter, thereby avoiding leaving any adhesive tape residue on the catheter.

where: 1—Base; 11—Fixing surface; 111—Groove; 112—Rotation shaft; 113—Snap; 2—Wing fixing portion; 21—Through hole; 22—Blocking portion; 23—Wing accommodation slot; 24—Pressing portion; 25—Protrusion; 26—Limiting column.

DETAILED DESCRIPTION

Figure 1:
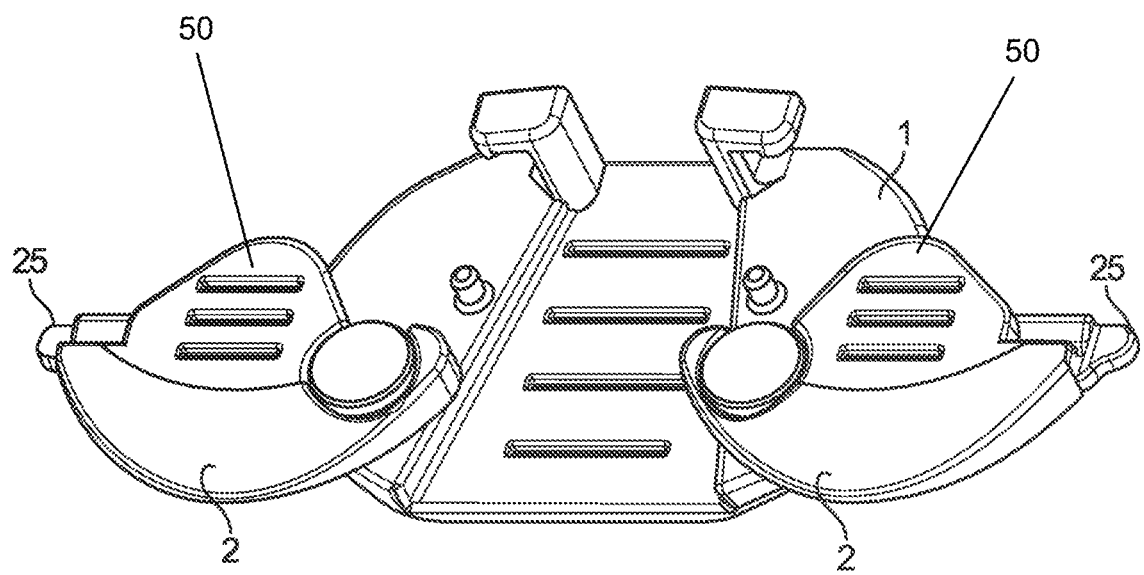
FIG. 1 is a schematic structural diagram of one embodiment of a catheter fixing assembly.
Figure 2:
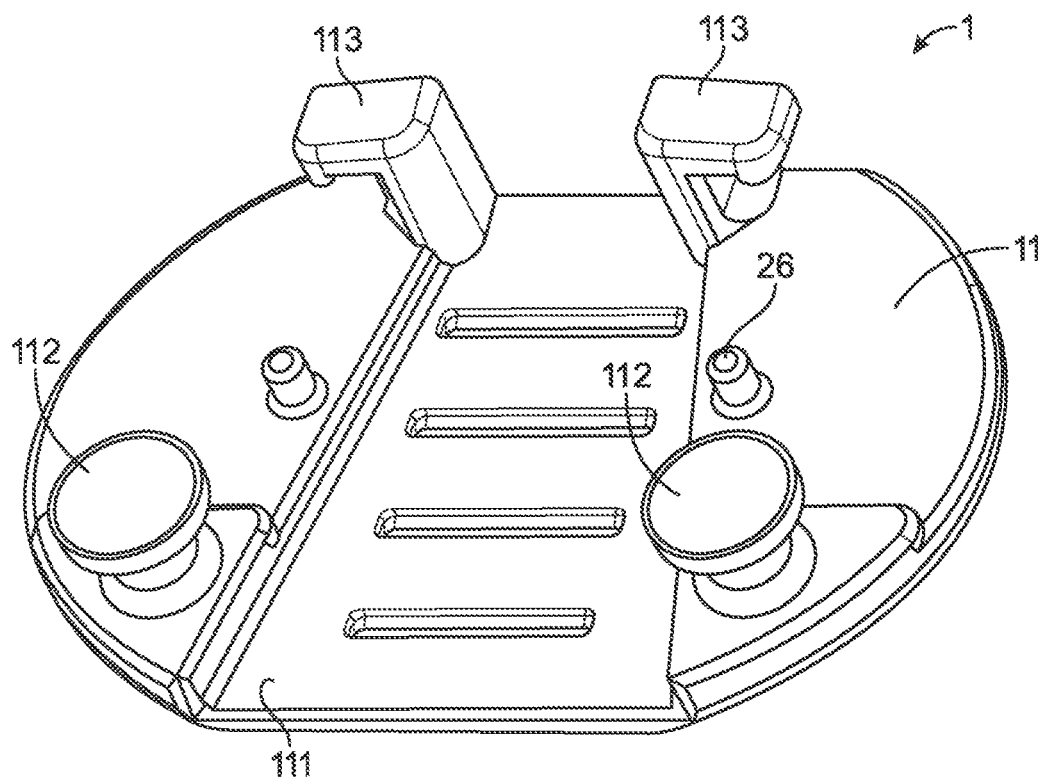
FIG. 2 is a schematic structural diagram of one embodiment of a base.

FIG. 1 is a schematic structural diagram of a catheter fixing assembly; and FIG. 2 is a schematic structural diagram of a base. As shown in FIG. 1 and FIG. 2, this embodiment provides a catheter fixing assembly comprising a base 1 and wing fixing portions 2. The base comprises an adhering surface and a fixing surface 11, the adhering surface is configured to adhere the base to the skin, and the wing fixing portions 2 are configured to detachably fix wings on the fixing surface 11.

It should be noted that in one embodiment the catheter fixing assembly is configured to fix a catheter. The catheter is provided with a catheter fixing wing. The catheter fixing wing comprises a fixing wing body and wings disposed on two sides of the fixing wing body.

In the catheter fixer, the wings of the catheter are fixed to the base by the wing fixing portions. An adhesive tape is disposed on one side of the base facing the skin, such that the adhesive tape is prevented from being adhered to the catheter, thereby avoiding leaving adhesive tape residue on the catheter.

FIG. 2 is a schematic structural diagram of a base. Referring to FIG. 1 and FIG. 2 together, in this embodiment, a central area on the fixing surface 11 of the base 1 is provided with a groove 111 configured to accommodate the fixing wing body, so that the wings can be carried by areas of the fixing surface 11 at two sides of the groove 111. By disposing the groove 111 on the fixing surface 11 of the base 1, when the catheter is placed on the base, the fixing wing body is located in the groove 111, and the wings are supported by the areas of the fixing surface 11 at two sides of the groove 111, so that the base can support the catheter fixing wings more stably.

In one embodiment, the shape and the size of the groove 111 are identical or similar to those of the fixing wing body, thus assisting fixation of the catheter by the groove 111.

Figure 3A:
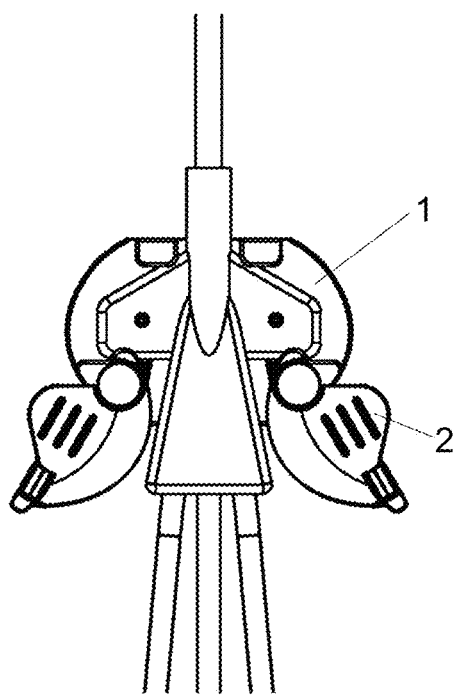
FIG. 3a is schematic structural diagram of a wing fixing portion when rotated to a first position.
Figure 3B:
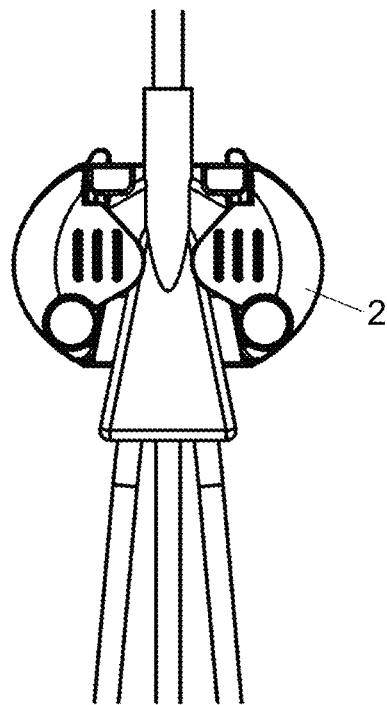
FIG. 3b is schematic structural diagram of a wing fixing portion when rotated to a second position.

In this embodiment, the base 1 further comprises rotation shafts 112 vertically disposed on the areas of the fixing surface 11 at two sides of the groove 111. The wing fixing portions 2 are rotatably connected to the rotation shafts 112. When the wing fixing portions 2 are rotated to a first position, as shown in FIG. 3a, the catheter fixing wings can be separated from the catheter fixing assembly; that is, the catheter fixing wings can be disassembled or assembled in this case. When the wing fixing portions 2 are rotated to a second position, as shown in FIG. 3b, the wing fixing portions 2 are superposed on and press against the wings to fix the catheter fixing wings on the fixing surface 11. The wing fixing portions 2 comprise bulbous portions 50 configured to overlay the catheter body in the second position.

The catheter is fixed when the wing fixing portions 2 are superposed on and press against the wings. The term "fixed" refers to the limiting the catheter from moving back and forth, left and right, up and down.

The number of the rotation shafts 112 should be consistent with the number of the wing fixing portions 2. The number of the wing fixing portions 2 should be consistent with the number of the wings on the catheter. Therefore, the number of the wing fixing portions 2 is two, and the number of the rotation shafts 112 is two.

Figure 4:
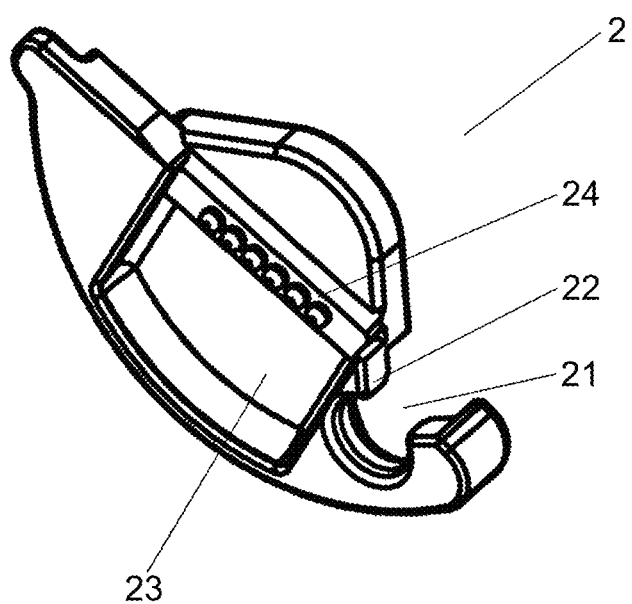
FIG. 4 is a schematic structural diagram of one embodiment of a wing fixing portion.

In this embodiment, as shown in FIG. 4, the wing fixing portion 2 is provided with a through hole 21, the diameter of the through hole 21 corresponds to the diameter of the rotation shaft 112, the through hole 21 has an opening at one side thereof, a distance of a projection of the opening on an axial section of the through hole 21 is smaller than the diameter of the rotation shaft 112. Moreover, during assembling, the rotation shaft 112 enters the wing fixing portion 2 through the opening by deformation of partial material of a blocking portion 22 under a force.

That the diameter of the through hole 21 corresponds to the diameter of the rotation shaft 112 refers to that the diameter of the through hole 21 is identical or similar to that of the rotation shaft 112.

A material of the wing fixing portion 2, at least at a part of the blocking portion 22 which is close to two ends of the opening, is an elastic material.

With the above structure, the rotation shaft 112 can enter the wing fixing portion by engagement, so as to avoid adding a rotation shaft mounting structure.

The material of the wing fixing portion 2 comprises polycarbonate (PC), polypropylene (PP), acrylonitrile-butadiene-styrene copolymer (ABS), or polyvinyl chloride (PVC) material. In one embodiment, the material of the wing fixing portion 2 is an elastic material.

In one embodiment, the wing fixing portion 2 is transparent so that a user can observe the fixing of the wing through the transparent wing fixing portion 2.

As shown in FIG. 2, in this embodiment, the base 1 is provided with snaps 113, the wing fixing portions 2 are provided with slots, and the snaps 113 are engaged to the slots when the wing fixing portions 2 are rotated to the second position, thus fixing the wing fixing portions 2 to the base 1.

In this embodiment, as shown in FIG. 1, the wing fixing portions 2 are further provided with protrusions 25 configured to be grabbed by the user to release the engagement between the snaps and the slots when the wing fixing portions 2 is away from the second position. The protrusion 25 can be disposed on a sidewall of the wing fixing portion 2, or disposed on an upper surface of the wing fixing portion 2, as long as it can be ensured that the protrusion 25 can be grabbed by the user when the wing fixing portion 2 is located in the second position.

In addition, the upper surface of the wing fixing portion 2 is further provided with a friction portion configured to be pressed and pushed toward a direction away from the second position for when the wing fixing portion 2 is to be away from the second position, such that the wing fixing portion 2 is away from the second position. The friction portion may be a groove, a protrusion, an adhesive surface, or the like, as long as a function of increasing the friction can be achieved.

In this embodiment, as shown in FIG. 4, one side of the wing fixing portion 2 facing the fixing surface 11 is provided with a wing accommodation slot 23 configured to accommodate the wing when the wing fixing portion 2 is rotated to the second position.

Further, the areas of the fixing surface at two sides of the groove 111 are provided with limiting columns 26. The wings are provided with round holes. When the wing fixing portions 2 are rotated to the second position, the limiting columns 26 match the round holes on the wings to limit positions of the wings.

Further, the wing accommodation slot 23 is provided with pressing portions 24, and a material of the pressing portions 24 is an elastic material. When the wing fixing portion 2 is rotated to the second position, the pressing portions 24 are in contact with the wing and pressed against the wing to generate elastic deformation, thus applying pressure to the wing. The pressing portions 24 are made of the elastic material, and thus can be used to press against wings having different thicknesses and in different sizes.

In one embodiment, there are multiple pressing portions 24. Orthogonal projections of the multiple pressing portions 24 disposed on the fixing surface are located in positions close to the groove 111. The multiple pressing portions 24 extend along an edge of the groove 111 when the wing fixing portion 2 is rotated to the second position, thus uniformly pressing against the wing.

In a case that the pressing portions 24 are simultaneously disposed both in the wing accommodation slots 23 and in the areas of the fixing surface at two sides of the groove 111. In one embodiment, the pressing portions 24 disposed in the wing accommodation slots 23 and the pressing portions 24 disposed in the areas of the fixing surface located at two sides of the groove 111 are arranged in a staggered manner, such that different positions of the wings may be pressed against.

In addition, the adhering surface is provided with an adhesive tape configured to adhere the base 1 to the skin. Specifically, the adhesive tape comprises a substrate, an adhesive, and a release paper disposed sequentially on the adhering surface. During use, the release paper is peeled off and the adhesive tape is adhered to the skin. The adhesive tape is adhered to the adhering surface by, for example, a 3M double-sided adhesive tape.

It can be understood that, the above embodiments are only exemplary embodiments employed for illustration of principles of the present invention, and do not limit the present invention. For those of ordinary skill in the art, various variations and modifications may be made without departing from the spirit and essence of the present invention, which variations and modifications are also considered as falling within the protection scope of the present invention.

What is claimed is:

1. A catheter fixing assembly for fixing a catheter to the skin of a patient, wherein the catheter comprises a catheter body, a first catheter wing extending from a first side of the catheter body, and a second catheter wing extending from a second side of the catheter body opposite the first side, the catheter fixing assembly comprising:
    a base, comprising:
        an adhering surface for adhering to the skin of the patient;
        a fixing surface, wherein a groove is defined in the fixing surface for accommodating the catheter body, and wherein the groove defines an axis;
        first and second rotation shafts extending from the fixing surface on first and second sides of the axis, respectively, the second side of the axis being opposite the first side of the axis; and
        first and second snaps on the first and second sides of the axis, respectively; and
    first and second wing fixing portions rotatably attached to the first and second rotation shafts, respectively, wherein the first and second wing fixing portions each comprise:
        a through hole for rotatably attaching to the respective first or second rotation shaft;
        a wing accommodation slot for accommodating one of the first or second catheter wings; and
        a tab for engaging with one of the first or second snaps;
    wherein the first and second wing fixing portions are rotatable about the first and second rotation shafts, respectively, to transition the catheter fixing assembly between:
        a first state in which the first wing fixing portion overlays the first catheter wing on the first side of the axis and the second wing fixing portion overlays the second catheter wing on the second side of the axis, thereby maintaining the catheter body in the catheter fixing assembly; and
        a second state in which the first and second wing fixing portions are rotated away from the first and second catheter wings, respectively, thereby allowing the catheter body to be removed from the catheter fixing assembly;
    wherein the first and second wing fixing portions are rotatable toward one another to transition the first and second wing fixing portions from the second state to the first state.

2. The catheter fixing assembly according to claim 1, wherein a diameter of the through hole of each of the first and second wing fixing portions is large enough to accommodate a diameter of the first and second rotation shafts, respectively.

3. The catheter fixing assembly according to claim 1, wherein the tabs of the first and second wing fixing portions are engaged by the first and second snaps, respectively, to lock the first and second wing fixing portions in the first state.

4. The catheter fixing assembly according to claim 3, wherein the first and second wing fixing portions each further comprise a protrusion configured to be grabbed to release the first and second wing fixing portions from the first state.

5. The catheter fixing assembly according to claim 1, wherein the wing accommodation slot of the first and second wing fixing portions are configured to accommodate the first and second catheter wings, respectively, when the first and second wing fixing portions are in the first state.

6. The catheter fixing assembly according to claim 5, wherein the first and second wing fixing portions each further comprise pressing portions positioned in the wing accommodation slot that are configured to engage the first and second catheter wings, respectively, and elastically deform under compression.

7. The catheter fixing assembly according to claim 1, further comprising an adhesive tape attached to the adhering surface of the base and configured to adhere the base to the skin.

8. The catheter fixing assembly according to claim 1, wherein the first and second wing fixing portions are non-overlapping in the first state.

9. A catheter fixing assembly for coupling a catheter to a patient, wherein the catheter comprises a catheter body, a first catheter wing extending from a first side of the catheter body, and a second catheter wing extending from a second side of the catheter body opposite the first side, wherein the catheter fixing assembly comprises:
    a base, comprising:
        a first surface for engaging the skin of the patient;
        a second surface defining a groove sized to receive the catheter body, wherein the groove defines an axis;
        first and second shafts extending from the second surface on first and second sides of the axis, respectively, the second side of the axis being opposite the first side of the axis; and
    first and second fixing wings rotatably coupled to the first and second shafts, respectively, wherein the first and second fixing wings are rotatable about the first and second shafts, respectively, to transition the catheter fixing assembly between:
        a first state in which the first fixing wing overlays the first catheter wing on the first side of the axis and the second fixing wing overlays the second catheter wing on the second side of the axis; and
        a second state in which the first and second fixing wings are rotated away from the first and second catheter wings, respectively;
    wherein the first and second fixing wings are rotatable toward one another to transition the first and second fixing wings from the second state to the first state.

10. The catheter fixing assembly according to claim 9, wherein the first and second fixing wings are non-overlapping in the first state.

11. The catheter fixing assembly according to claim 9, wherein the base further comprises first and second snaps extending from the second surface on the first and second sides of the axis, respectively, and wherein the first and second snaps are configured to rotatably receive the first and second fixing wings, respectively.

12. The catheter fixing assembly according to claim 11, wherein the first and second snaps engage the first and second fixing wings, respectively, to maintain the first and second fixing wings in the first state.

13. The catheter fixing assembly according to claim 11, wherein the first and second snaps comprise C-shaped snaps.

14. The catheter fixing assembly according to claim 9, wherein the first and second fixing wings comprise bulbous portions configured to overlay the catheter body in the first state.

15. A catheter fixing assembly for coupling a catheter to a patient, wherein the catheter comprises a catheter body, a first catheter wing extending from a first side of the catheter body, and a second catheter wing extending from a second side of the catheter body opposite the first side, wherein the catheter fixing assembly comprises:
  a base defining an axis, wherein the base comprises:
    a surface; and
    first and second shafts extending from the surface on first and second sides of the axis, respectively, the second side of the axis being opposite the first side of the axis; and
  first and second fixing wings rotatably coupled to the first and second shafts, respectively, wherein the first and second fixing wings are rotatable about the first and second shafts, respectively, to transition the catheter fixing assembly between:
    a first state in which the first fixing wing overlays the first catheter wing and the second fixing wing overlays the second catheter wing, wherein the first and second fixing wings are non-overlapping in the first state; and
    a second state in which the first and second fixing wings are rotated away from the first and second catheter wings, respectively;
  wherein the first and second fixing wings are rotatable toward one another to transition the first and second fixing wings from the second state to the first state.

16. The catheter fixing assembly according to claim 15, wherein the base further comprises first and second snaps extending from the first and second sides of the axis, respectively, and wherein the first and second snaps are configured to rotatably receive the first and second fixing wings, respectively.

17. The catheter fixing assembly according to claim 16, wherein the first and second snaps engage the first and second fixing wings, respectively, to maintain the first and second fixing wings in the first state.

18. The catheter fixing assembly according to claim 16, wherein the first and second snaps comprise C-shaped snaps.

19. The catheter fixing assembly according to claim 15, wherein the first and second fixing wings comprise bulbous portions configured to overlay the catheter body in the first state.

* * * * *